US00PP34122P2

(12) United States Plant Patent
Trees

(10) Patent No.: US PP34,122 P2
(45) Date of Patent: Apr. 12, 2022

(54) ***LANTANA* PLANT NAMED 'SAILAN003'**

(50) Latin Name: *Lantana camara*
Varietal Denomination: SAILAN003

(71) Applicant: Sakata Seed America, Inc., Morgan Hill, CA (US)

(72) Inventor: Scott C. Trees, Arroyo Grande, CA (US)

(73) Assignee: SAKATA SEED AMERICA, INC., Morgan Hill, CA (US)

( * ) Notice: Subject to any disclaimer, the term of this patent is extended or adjusted under 35 U.S.C. 154(b) by 0 days.

(21) Appl. No.: 17/496,183

(22) Filed: Oct. 7, 2021

(51) Int. Cl.
*A01H 5/02* (2018.01)
*A01H 6/86* (2018.01)

(52) U.S. Cl.
USPC ..... Plt./227
CPC ..... *A01H 6/86* (2018.05)

(58) Field of Classification Search
USPC ..... Plt./227
CPC ..... A01H 6/86; A01H 5/02
See application file for complete search history.

*Primary Examiner* — Keith O. Robinson
(74) *Attorney, Agent, or Firm* — Weatherly IP Solutions, LLC; James M. Weatherly

(57) ABSTRACT

A new *Lantana* plant designated 'SAILAN003' particularly distinguished by semi-mounding growth habit, red flower color; and excellent heat tolerance is disclosed.

2 Drawing Sheets

Genus and species: *Lantana camara.*
Variety denomination: 'SAILAN003'.

BACKGROUND

The present invention relates to a new and distinct cultivar of *Lantana* plant botanically known as *Lantana camara* and hereinafter referred to by the cultivar name 'SAILAN003'.

The new cultivar originated in a controlled breeding program in Guadalupe, Calif. during June 2014. The objective of the breeding program was the development of *Lantana* cultivars with a semi-mounded growth habit, yellow flower color and excellent heat tolerance.

The new *Lantana* cultivar is the result of cross-pollination. The female (seed) parent of the new cultivar is the proprietary *Lantana camara* breeding selection coded '3460', not patented, characterized by its medium red colored inflorescences, medium green colored foliage, and moderately vigorous, trailing growth habit. The male (pollen) parent of the new cultivar is 'Lola', not patented, characterized by its bright yellow colored inflorescences, medium green colored foliage, and vigorous, semi-upright growth habit. The new cultivar was selected as a single flowering plant within the progeny of the above stated cross-pollination during May 2015 in a controlled environment in Guadalupe, Calif.

Asexual reproduction of the new cultivar by terminal stem cuttings since May 2015 in Guadalupe, Calif. and Arroyo Grande, Calif. has demonstrated that the new cultivar reproduces true to type with all of the characteristics, as herein described, firmly fixed and retained through successive generations of such asexual propagation.

SUMMARY

The following characteristics of the new cultivar have been repeatedly observed and can be used to distinguish 'SAILAN003' as a new and distinct cultivar of *Lantana* plant:

1. Semi-mounding growth habit;
2. Red flower color; and
3. Excellent heat tolerance.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'SAILAN003'. The approximately 4-month-old plants were grown in 4.5-inch pots for approximately 2 weeks, then transplanted into 6-inch pots and grown for an additional 12 weeks in a greenhouse in West Chicago, Ill. Plants were given one pinch one week after the first transplant.

DETAILED BOTANICAL DESCRIPTION

Figure 1:
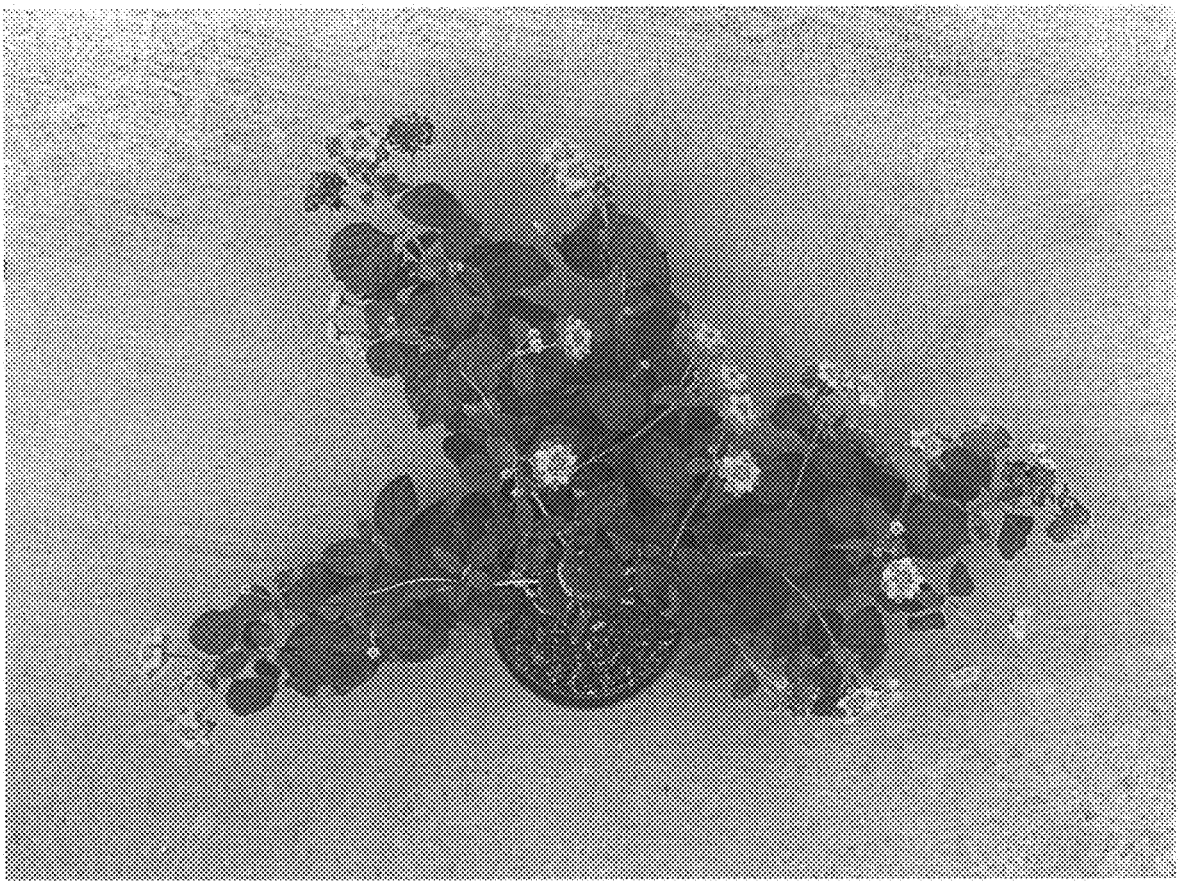
FIG. 1 illustrates a side view of the overall growth and flowering habit of 'SAILAN003'.
Figure 2:
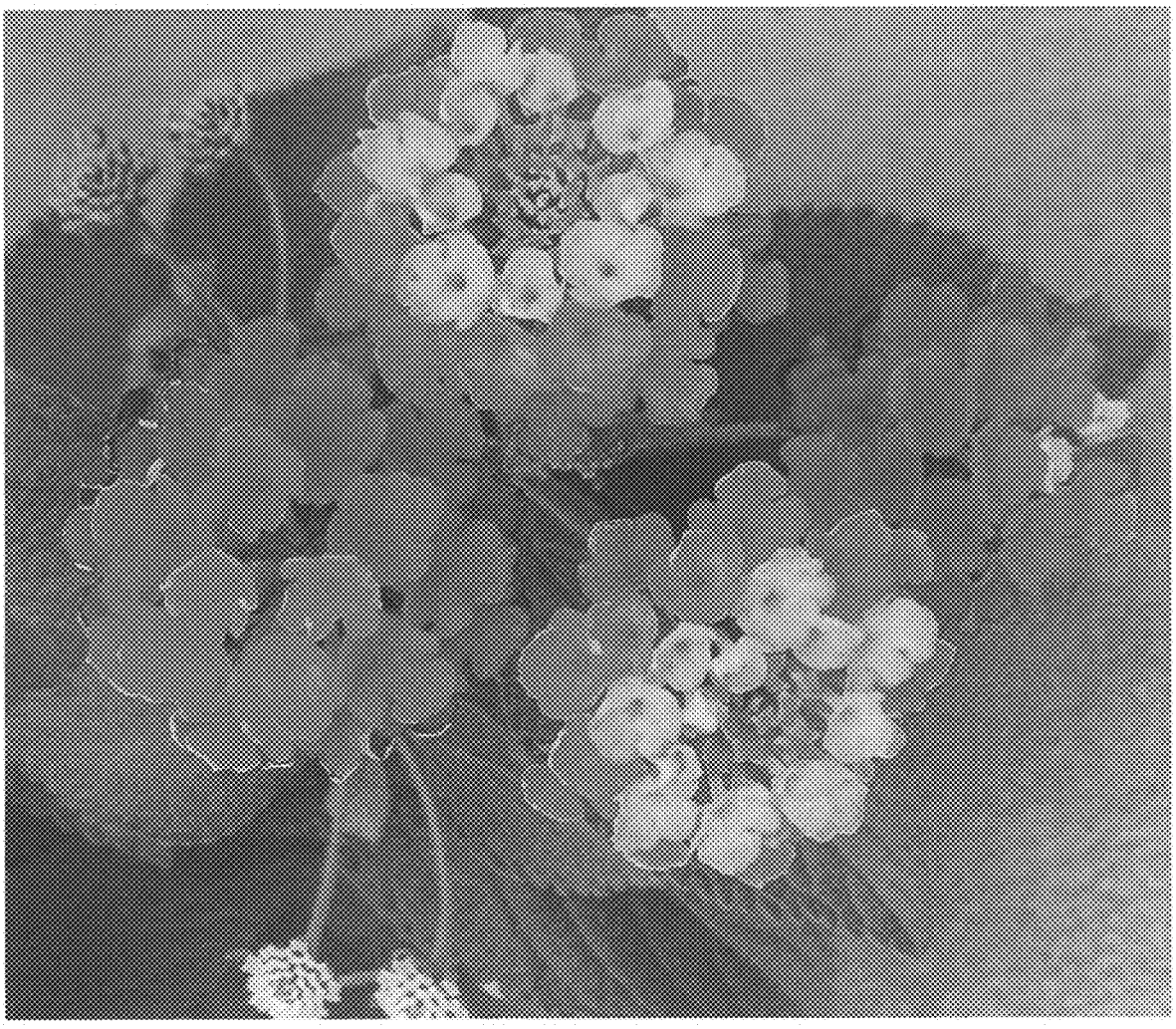
FIG. 2 illustrates a close-up view of an individual inflorescence of 'SAILAN003'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used.

The following descriptions and measurements were collected in February of 2021 and obtained from plants grown four months from transplant into 4-inch pots from rooted cuttings in Salinas, Calif., under greenhouse conditions.

Botanical classification:

*Genus and species.*—*Lantana camara.*

*Variety.*—'SAILAN003'.

*Parentage.*—Female parent: '3460', not patented. Male parent: 'Lola', not patented.

Growth:

*Type cutting.*—Terminal stem.

*Time to initiate roots.*—Approximately 7 to 11 days.

*Time to produce a rooted cutting.*—Approximately 35 to 42 days.

*Root description.*—Fibrous; woody.

*Rooting habit.*—Freely branching. The terminal 1.0 to 1.5 inches of an actively growing stem was excised. The vegetative cuttings were propagated in five to six weeks. The base of the cuttings were dipped for 1 to 2 seconds in a 1:9 solution of Dip 'N Grow (1 solution:9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24C.

Plant description:

*Commercial crop time.*—Approximately 6 to 7 weeks from a rooted cutting to finish in a 10 cm pot.

*Growth habit and general appearance.*—Moderately vigorous, semi-upright.

*Height from soil level to top of plant plane.*—Approximately 10.0 cm.

*Width.*—Approximately 65.0 cm.

*Branching habit.*—Freely branching, pinching enhances branching.

*Quantity of lateral branches per plant.*—1 main and 2 lateral.

Branch:

*Shape.*—Square in cross section.

*Strength.*—Strong, becomes woody with age.

*Length.*—Approximately 40.0 cm main branch. Approximately 3.0 cm between soil and first node

*Diameter.*—7.0 mm.

*Length of central internode.*—Approximately 3.5 cm.

*Texture.*—Densely pubescent, short rough pubescence.

*Gland color.*—Colorless, transparent.

*Color of young stem.*—144A (Strong Yellow Green).

*Color of mature stem.*—Closest to 199B (Light Olive Brown).

Foliage description:

*Quantity of leaves per lateral branch.*—Approximately 30 or more.

*Fragrance.*—None.

*Form.*—Simple.

*Arrangement.*—Opposite.

*Aspect.*—Perpendicular to or acute angle to stem.

*Shape.*—Ovate.

*Margin.*—Serrate.

*Apex.*—Acuminate.

*Base.*—Obtuse

*Venation pattern.*—Entire.

*Length of mature leaf.*—Approximately 9.0 cm.

*Width of mature leaf.*—Approximately 5.2 cm.

*Texture of upper surface.*—Scabrous; rough.

*Texture of lower surface.*—Scabrous and glandular pubescent along venation.

*Gland color.*—Not observed.

*Vein color upper.*—145A (Strong Yellow Green).

*Vein color lower.*—145B (Light Yellow Green).

*Color of upper surface.*—Closest to but darker than NN137A (Greyish Olive Green).

*Color of lower surface.*—Closest to but darker than NN137D (Greyish Olive Green).

Petiole:

*Length.*—Approximately 12.0 mm.

*Diameter.*—Approximately 1.5 mm.

*Texture.*—Lightly Pubescent; NN155D (White).

*Gland color.*—Transparent.

*Color.*—Closest to but lighter than 146B (Moderate Yellow Green).

Flowering description:

*Flowering habit.*—'SAILAN003' is freely flowering under outdoor growing conditions with substantially continuous blooming from spring through autumn and year-round in greenhouse environment.

*Lastingness of individual inflorescence on the plant.*—Approximately 7 to 10 days from first color of outer buds to dropping of last flower.

Inflorescence description:

*Type.*—Umbel.

*Quantity per plant.*—Approximately 30.

*Fragrance.*—Strong, spicy.

*Aspect.*—Facing upward or outward.

*Height.*—Approximately 2.5 cm.

*Width.*—Approximately 4.0 cm.

*Quantity of fully open flowers per inflorescence.*—Approximately 40.

Peduncle:

*Strength.*—Strong; flexible.

*Shape.*—Square in cross section.

*Aspect.*—Acute angle to stem.

*Length.*—Approximately 7.3 on mature influences.

*Diameter.*—Approximately 2.0 mm.

*Texture.*—Lightly scabrous.

*Gland color.*—Transparent.

*Color.*—143B (Strong Yellow Green).

Flower description:

*Type.*—Salverform.

Bud:

*Rate of opening.*—Generally takes 1 to 2 days for bud to progress from first color to fully open flower. Buds open in progression from the margin to the center of the inflorescence.

*Quantity of unopened inflorescences per plant.*—Approximately 40 of various stages at time of collections.

*Shape.*—Elongated, rectangular at apex.

*Length.*—Approximately 9.0 mm.

*Diameter.*—Approximately 3.0 mm.

*Color.*—Color changes depending on maturity, all flowers will be red at maturity. Visible colors range from 2D (Pale Greenish Yellow) at youngest, to 17B (Vivid Yellow), to N25A (Strong Orange), to 42B (Vivid Reddish Orange) at oldest.

Corolla:

*Depth*.—Approximately 1.0 mm.

*Diameter*.—Approximately 12.0 mm.

Petals:

*Quantity*.—4.

*Description*.—Non-imbricate, non-symmetrical petals. Petals are fused at base forming a corolla tube.

*Shape*.—Obovate.

*Appearance*.—Dull.

*Aspect*.—Cupped.

*Margin*.—Entire, slightly ruffled.

*Apex*.—Obtuse; rounded.

*Length of upper petal from throat*.—Approximately 6.0 mm.

*Width of upper petal*.—Approximately 6.0 mm.

*Length of lateral petals from throat*.—Approximately 5.0 mm.

*Width of lateral petals*.—Approximately 3.5 mm.

*Length of lower petal from throat*.—Approximately 4.5 mm.

*Width of lower petal*.—Approximately 7.0 mm.

*Texture of upper and lower surface*.—Glabrous.

*Gland color*.—Not observed.

*Color of upper surface*.—Color changes depending on maturity, all flowers will be red at maturity. Red (Mature): Closest N45A (Moderate Red). Orange: N25A (Strong Orange); and N30A (Vivid Reddish Orange). Yellow: 17B (Vivid Yellow).

*Color of lower surface*.—Color changes depending on maturity, all flowers will be red at maturity. Red (Mature): 35B (Moderate Reddish Orange). Orange: Closest to 168C (Moderate Orange). Yellow: 13B (Brilliant Yellow).

Corolla tube:

*Length*.—Approximately 1.2 cm.

*Diameter at midpoint*.—Approximately 2.0 mm.

*Texture of inner and outer surface*.—Glabrous.

*Pubescence color*.—None.

*Color of inner surface*.—5C (Light Greenish Yellow at base and hints of 14B (Vivid Yellow) near throat that blend into corolla.

*Color of outer surface*.—12B (Brilliant Yellow) with slight N34C (Moderate Red) on more mature flowers.

Calyx:

*Shape*.—Tubular with two broadly acute tips.

*Length*.—Approximately 3.0 mm.

*Diameter*.—Approximately 1.5 mm.

*Texture*.—Glabrous.

*Gland color*.—Transparent.

*Color of inner and outer surfaces*.—145C (Light Yellow Green).

Bracts:

*Quantity per flower*.—1 per flower.

*Shape*.—Linguate

*Length*.—Approximately 10.0 mm.

*Width*.—Approximately 2.0 mm.

*Texture of upper and lowers surface*.—Slightly pubescent.

*Color of upper and lower surfaces*.—141A (Deep Yellow Green) at apex lightening to 143C (Strong Yellow Green) at base.

Reproductive organs:

*Androecium*.—Stamen quantity: 4 per flower, adnate to corolla tube. Stamen length: Approximately 1.0 mm. Anther shape: Bilobed, ovoid. Anther length: Approximately less than 1.0 mm. Anther color: 163A (Deep Orange Yellow). Pollen amount: Abundant. Pollen Color: 2C (Light Yellow Green)

*Gynoecium*.—Pistil quantity: 1 per flower. Pistil length: Approximately 3.5 mm. Stigma shape: Funnel. Stigma length: Less than 1.0 mm. Stigma color: N144C (Strong Yellow Green). Style length: Approximately 2.5 mm. Style color: 150D (Light Yellow Green). Ovary diameter: Approximately 1.0 mm. Ovary color: 144C (Strong Yellow Green).

Seed and fruit production: Neither seed nor fruit production has been observed.

Disease and pest resistance: Resistance to pathogens and pests common to *Lantana* has not been observed.

COMPARISON OF 'SAILAN003' WITH PARENTAL LINES AND KNOWN VARIETY

'SAILAN003' is distinguished from the parental lines as described in Table 1.

TABLE 1

Comparison with Parental Lines

| Trait | Variety 'SAILAN003' | Female parent '3460' | Male parent 'Lola' |
|---|---|---|---|
| Inflorescense color | Red | Medium Red | Bright yellow |
| Growth habit | Semi-mounding | Trailing | Semi-upright |

'SAILAN003' can be compared to the commercial *Lantana* variety 'Bant Reda09' (U.S. Plant Pat. No. 20,531). Differences between the varieties are described in Table 2.

TABLE 2

Comparison with Similar Variety

| | 'SAILAN003' | 'Bant Reda09' |
|---|---|---|
| Leaf Color - Upper Surface | Closest to but darker than RHS NN137A | Darker than RHS 147A |
| Peduncle Color | RHS 143B | RHS 144A |
| Corolla Tube - Color of inner surface | 5C (Light Greenish Yellow at base and hints of 14B (Vivid Yellow) near throat that blend into corolla. | RHS 10B |

I claim:

1. A new and distinct variety of *Lantana* plant designated 'SAILAN003' as illustrated and described herein.

* * * * *